United States Patent
Das et al.

(10) Patent No.: US 11,221,318 B2
(45) Date of Patent: Jan. 11, 2022

(54) ADSORPTION/DESORPTION-BASED SENSOR FOR VOLATILE ORGANIC COMPOUNDS (VOCS)

(71) Applicant: International Business Machines Corporation, Armonk, NY (US)

(72) Inventors: Siddhartha Das, Sunnyvale, CA (US); Andrea Fasoli, San Jose, CA (US); Luisa Dominica Bozano, Los Gatos, CA (US)

(73) Assignee: International Business Machines Corporation, Armonk, NY (US)

( * ) Notice: Subject to any disclaimer, the term of this patent is extended or adjusted under 35 U.S.C. 154(b) by 393 days.

(21) Appl. No.: 16/521,018

(22) Filed: Jul. 24, 2019

(65) Prior Publication Data

US 2021/0025861 A1    Jan. 28, 2021

(51) Int. Cl.
    *G01N 33/00*    (2006.01)
(52) U.S. Cl.
    CPC ..... *G01N 33/0026* (2013.01); *G01N 33/0006* (2013.01); *G01N 33/0014* (2013.01)
(58) Field of Classification Search
    CPC ........... G01N 33/0026; G01N 33/0006; G01N 33/0014
    See application file for complete search history.

(56) References Cited

U.S. PATENT DOCUMENTS

| | | | |
|---|---|---|---|
| 5,448,905 A | * | 9/1995 | Stetter ................ G01N 33/0026 73/23.21 |
| 9,983,124 B2 | | 5/2018 | Wang et al. |
| 2018/0024058 A1 | | 1/2018 | Kim et al. |
| 2018/0224443 A1 | | 8/2018 | Swager et al. |

FOREIGN PATENT DOCUMENTS

CN    109078489 A    12/2018

OTHER PUBLICATIONS

Chang, Y. et al. Detection of Volatile Organic Compounds by Self-assembled Monolayer Coated Sensor Array with Concentration-independent (Year: 2016).*
Britt et al., Highly Efficient Separation of Carbon Dioxide by a Metal-Organic Framework Replete with Open Metal Sites, Proceedings of the National Academy of Science (PNAS) 106(49):20637-20640 (2009).
Campbell and Dinca, Metal-Organic Frameworks as Active Materials in Electronic Sensor Devices, Sensors 17 (1108):1-11 (2017).
Kreno et al., Metal-Organic Framework Materials as Chemical Sensors, Chemical Reviews 112:1105-1125 (2012).
Shyju et al., Gas Sensing Properties of Metal Oxide Thin Films, Archives of Applied Science Research 4(5):2149-2151 (2012).

* cited by examiner

*Primary Examiner* — Christopher Adam Hixson
(74) *Attorney, Agent, or Firm* — Karen Canaan; CanaanLaw, P.C.

(57) ABSTRACT

Provided is a system for detection and discrimination of gases, such as volatile organic compounds (VOCs), in a sample comprising two chambers, a first chamber equipped with a crystalline microporous material (CMM) and a second chamber equipped with a gas detector. A gas sample is introduced first into the second chamber for detection by the gas detector and is then re-routed to the first chamber for adsorption/desorption on the CMM. The gas detector in the second chamber produces electronic signals that correspond to the adsorption/desorption profile for the gas, which allows for discrimination of the gas in the sample from other possible gas samples.

27 Claims, 9 Drawing Sheets

ADSORPTION/DESORPTION-BASED SENSOR FOR VOLATILE ORGANIC COMPOUNDS (VOCS)

TECHNICAL FIELD

This invention relates generally to gas sensors and more specifically to an adsorption/desorption-based gas sensor system that can discriminate and identify a wide range of volatile organic compounds (VOCs).

BACKGROUND OF THE INVENTION

To be effective, VOC sensors must have high selectivity, i.e., the ability to discriminate between two VOCs that are chemically and structurally very similar; and high sensitivity, i.e., the ability to detect very low concentrations of a single VOC. Gas chromatography-mass spectrometry (GCMS) and infra-red spectrophotometry (also known as Fourier-transform infrared spectroscopy or FTIR) instruments are selective tools for VOC detection; however, these expensive, bulky, and maintenance-heavy instruments are limited to benchtop analytics. Electrochemical (EC) sensors are sensitive and selective for a handful of low molecular weight gases that are highly redox active (e.g., $SO_2$, $NO_2$, $O_2$, CO, etc.), but suffer from a lack of selectivity with VOCs, which are organic compounds with 6-12 carbons (e.g., ethanol, toluene, benzene). Quartz crystal microbalance (QCM) sensors are a class of sensitive piezoelectric sensors that are capable of discriminating between two VOCs based upon the molecular weight (MW) of the VOCs; however, this type of discrimination is not effective where two VOCs have the same MW.

Metal oxide semiconductor (MOS) sensors, which are portable and low-cost, are the most widely used gas sensors. While MOS sensors have high sensitivity for VOCs (ppb level for certain VOCs), MOS sensors lack sufficient selectivity.

There remains a need in the art for a portable, cost-effective gas sensor that is highly sensitive and selective and that can be used to detect a wide range of VOCs.

SUMMARY OF THE INVENTION

The present invention overcomes the need in the art by providing a sensitive and selective adsorption/desorption-based gas sensor system comprising at least one gas detector and at least one microporous material.

In one aspect of the invention, there is provided a method of detecting at least one volatile organic compound (VOC), comprising the steps of: providing a first chamber and a second chamber connected in series, wherein the first chamber contains a porous material that adsorbs an amount of the at least one VOC and the second chamber contains a detector for detecting a presence and concentration of the at least one VOC; introducing a gas without the at least one VOC into the second chamber while bypassing the first chamber; establishing a first baseline electronic signal corresponding to the gas without the at least one VOC, wherein the first baseline electronic signal is generated by the detector in the second chamber; introducing at least one VOC into the second chamber while bypassing the first chamber; detecting, over time, the presence of the at least one VOC in the second chamber by establishing a second electronic signal corresponding to the concentration of the at least one VOC in the second chamber, wherein the second electronic signal is generated by the detector in the second chamber; re-routing the gas so that it is directed into the first chamber, wherein an amount of the at least one VOC is adsorbed onto the porous material in the first chamber; directing the gas out of the first chamber into the second chamber; and monitoring, over time, a third electronic signal corresponding to a change in the concentration of the VOC in the first chamber resulting from adsorption of some or all of the amount of the at least one VOC and subsequent desorption of some or all of the amount of at least one VOC in the first chamber, wherein the third electronic signal is generated by the detector in the second chamber; and comparing the third electronic signal with electronically stored signals for known VOCs to identify the at least one VOC, wherein the third electronic signal reaches an extremum as the amount of the at least one VOC adsorbed in the first chamber no longer increases, and upon desorption of the at least one VOC from the first chamber, the third electronic signal approaches a background level equal to a maximum value of the second electronic signal.

In another aspect, each of the steps are carried out in turn.

In one embodiment of the invention, there is provided a system comprising a first chamber comprising a crystalline microporous material for adsorbing and desorbing at least one gas; a second chamber comprising a gas detector for detecting and measuring a concentration of the least one gas; a pass-through line comprising an input, a first line, and a second line, wherein the first line bypasses the first chamber and passes through the second chamber and the second line passes through the first and second chambers, wherein upon entry of the at least one gas into the system, the at least one gas is routed to the second chamber via the input and the first line, wherein the gas detector in the second chamber generates a signal over time corresponding to the concentration of the at least one gas in the second chamber, and wherein the at least one gas is rerouted from the second chamber to the first chamber via the input and the second line, wherein an amount of the at least one gas is first adsorbed onto the crystalline microporous material and then some or all of the amount of the at least one gas is desorbed from the crystalline microporous material, and the gas detector in the second chamber generates a signal over time corresponding to the concentration of the at least one gas in the first chamber that is not adsorbed onto the crystalline microporous material.

In another embodiment of the invention, there is provided a system comprising: a first chamber comprising a crystalline microporous material for adsorbing and desorbing at least one gas; a second chamber comprising a gas detector for detecting and measuring a concentration of the least one gas; a pass-through line comprising, an input, an output, a first line that bypasses the first chamber and runs from the input to the output via the second chamber, and a second line that passes from the input through the first and second chambers to the output, wherein upon entry of the at least one gas into the system via the input, the at least one gas is (i) routed to the second chamber via the first line, wherein the at least one gas is detected, and (ii) rerouted to the first chamber via the second line, wherein an amount of the at least one gas is adsorbed onto the crystalline microporous material and then some or all of the amount of the at least one gas is desorbed from the microporous crystalline structure, wherein the gas detector in the second chamber produces a first signal corresponding to the concentration of the at least one gas in the first chamber, a second signal corresponding to the amount of the at least one gas adsorbed onto the crystalline microporous material in the first chamber, and a third signal corresponding to the amount of the at least one gas desorbed from the crystalline microporous material in first chamber, wherein the three signals together produce an adsorption/desorption profile for the at least one gas to enable identification of the at least one gas.

In a further embodiment, the porous or crystalline microporous material is selected from the group consisting of a metal organic framework, a covalent organic framework, a metal-organic polyhedral, a coordination polymer, zeolites, microporous carbonaceous materials, and combinations thereof.

In another embodiment, the porous or crystalline microporous material comprises a metal organic framework.

In a further embodiment, the first chamber further comprises a heating plate.

In another embodiment, the porous or crystalline microporous material in the first chamber is recycled by heating the first chamber to a temperature that does not alter the structure of the porous or microporous crystalline material.

In a further embodiment, the detector in the second chamber is selected from the group consisting of a gas chromatography mass spectrometer, an infra-red spectrophotometer, an electrochemical sensor, a quartz crystal microbalance, a metal oxide semiconductor, and combinations thereof.

In another embodiment, the detector or gas detector in the second chamber comprises a metal oxide thin film.

In a further embodiment, the metal oxide thin film in the second chamber is deposited on a membrane heater fitted with microelectrodes.

In another embodiment, the at least one gas is a volatile organic compound.

Additional aspects and embodiments of the invention will be provided, without limitation, in the detailed description of the invention that is set forth below.

DETAILED DESCRIPTION OF THE INVENTION

Figure 1:
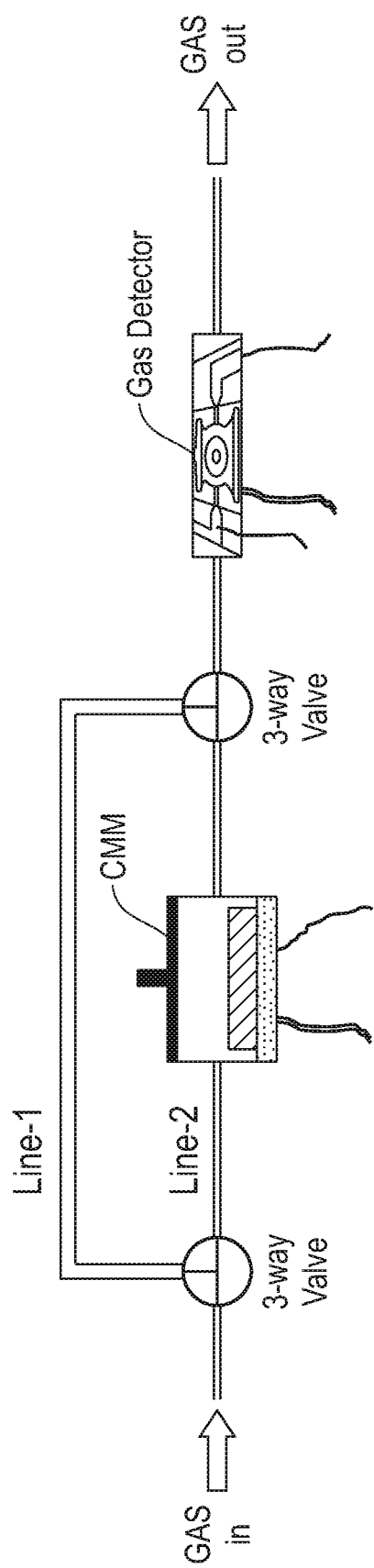
FIG. 1 is a schematic diagram of an adsorption/desorption (AD) sensor as described herein.

Set forth below is a description of what are currently believed to be preferred embodiments of the claimed invention. Any alternates or modifications in function, purpose, or structure are intended to be covered by the claims of this application. As used in this specification and the appended claims, the singular forms "a," "an," and "the" include plural referents unless the context clearly dictates otherwise. The terms "comprises" and/or "comprising," as used in this specification and the appended claims, specify the presence of stated features, integers, steps, operations, elements, and/or components, but do not preclude the presence or addition of one or more other features, integers, steps, operations, elements, components, and/or groups thereof.

As used herein, the term "volatile organic compound" or "VOC" means any organic chemical compound (either liquid or solid) that evaporates under normal indoor atmospheric conditions of temperature and pressure. Examples of VOCs include, without limitation, acetone, benzene, bromodichloromethane, bromomethane, butane, butanol, carbon disulfide, carbon tetrachloride, chloroform, chloromethane, dibromochloropropane, dibromomethane, dichlorobenzenes, dichloropropenes, diethyl ether, ethanol, ethyl benzene, ethylene dibromide, formaldehyde, gasoline, hexachlorobutadiene, hexachloroethane, hexane, hydrazines, isopropanol, n-propanol, methane, methanol, methyl chloride, methyl mercaptan, nitrobenzene, propane, styrene, toluene, trichloroethylene (TCE), tetrachloroethylene (PERC), trichloropropane, vinyl chloride, and xylenes.

As used herein, the terms "gas" and "gases" are meant to refer to all gaseous chemicals and chemical compounds, including gaseous VOCs and gaseous chemicals and/or chemical compounds that are not VOCs. The VOCs defined herein are understood to be included in the term "gas" and "gases." Examples of gases that are not VOCs include, without limitation, air, oxygen, nitrogen, carbon monoxide, carbon dioxide, carbonic acid, metallic carbides, metallic carbonates, and ammonium carbonate.

As used herein, the term "gas line" and "gas lines" refers to a pipe or hose intended to transfer a gas (including VOCs) from one source (e.g., a main supply of the gas) to another source (e.g., a device and/or a portion of a device).

As used herein, the terms "sensor," "gas sensor," and "gas sensor system" are used interchangeably to refer to a system that differentiates between two or more gases.

As used herein, the terms "detector" and "gas detector" refer to a device that is capable of identifying gases, but is not used to differentiate between two or more gases.

As used herein, the term "metal organic framework" or "MOF" refers to materials that are made from a combination of metal ions and organic ligands, which together form a metal-organic framework that contains pores. The pores of a MOF may range from 0.5 nm to 10 nm, depending on the metal ion/organic ligand combination used for the MOF. Owing to high surface area (>1000 m$^2$/g), MOFs have high affinity and capacity for adsorption of gases including VOCs.

The adsorption/desorption (AD) sensors described herein are sensors that exhibit high sensitivity (e.g., ppb-level sensitivity) and high selectivity in the detection and discrimination of low concentration VOCs that are similar in chemical properties, molecular weights, and/or size. Examples of such similar VOCs include alcohols that vary by only one carbon center, such as:

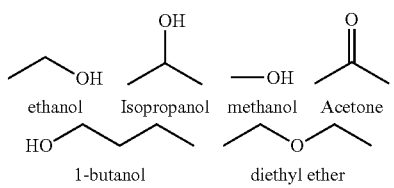

In one embodiment, which is shown schematically in FIG. 1, the AD sensor comprises a first chamber comprising a known amount of a crystalline microporous material (CMM) and a heating plate; a second chamber comprising a gas detector, a membrane heater, and interdigitated microelectrodes; a first gas line (also referred to herein as "line 1") that directly reaches the gas detector chamber; and a second gas line (also referred to herein as "line 2") that is parallel to the first gas line and that passes through the CMM chamber and arrives at the detector chamber.

In another embodiment, the heating plate in the first chamber is a mm-sized heating plate. In a further embodiment, the gas detector in the second chamber is deposited on the membrane heater. In another embodiment, a valve controls the gas flow through the first and second gas lines. In a further embodiment, the valve is a three-way valve. In another embodiment, the AD sensor is portable and thus applicable to field applications. The small size of the CMM chamber and the gas detector allows the AD sensor to be fitted into a hand-held device.

In a further embodiment, the CMM is any microporous material that exhibits permanent porosity owing to a crystal structure. Examples of CMMs that may be used in the first chamber of the AD sensor include, without limitation, MOFs, covalent organic frameworks (COFs), metal-organic polyhedrals (MOPs), coordination polymer (CP), zeolites, microporous carbonaceous materials, and combinations thereof. The amount of CMM placed into the CMM chamber will depend on the CMM used. In one embodiment, a MOF is used as the CMM in an appropriate concentration for the chamber, which may range from 1 µg to 100 mg. In the Examples, 7 mg of the MOF, Mg-MOF-74, is used (Examples 1 and 4) and 25 mg of the MOF, Al-MIL-53, is used (Examples 2, 3, and 5); however, it is to be understood that these amounts are appropriate for the CMM chamber used in the Examples and that the amount of MOF used in any other CMM chamber will be dependent upon the components of the AD sensor system and its capacity.

In another embodiment, the gas detector is any high sensitivity gas detector. Examples of gas detectors that may be used in the second chamber of the AD sensor include, without limitation, gas chromatography mass spectrometers (GCMSs), Fourier-transform infrared spectrometers (FTIRs), electrochemical (EC) sensors, quartz crystal microbalances (QCMs), metal oxide semiconductor (MOS) detectors, and combinations thereof. In a further embodiment, the MOS detector is a semiconducting metal oxide thin film (MOxTF). Examples of metal oxides that may be used for a MOS detector, including a MOxTF, include, without limitation, aluminum oxide ($Al_2O_3$), ceric dioxide ($CeO_2$), cuprous oxide ($Cu_2O$), cupric oxide (CuO), copper peroxide ($CuO_2$), copper(III) oxide ($Cu_2O_3$), indium oxide ($In_2O_3$), ferric oxide ($Fe_2O_3$), iron(II) oxide FeO, iron(II,III) oxide ($Fe_3O_4$), manganese dioxide ($MnO_2$), tin(IV) oxide ($SnO_2$), titanium dioxide ($TiO_2$), tungsten trioxide ($WO_3$), zinc oxide (ZnO), and combinations thereof.

In another embodiment, a gas without any VOC is passed through line 1, bypassing line 2. The electronic signal generated by the gas sensor establishes a baseline value for the system. The VOC-free gas may be dry air (i.e., a mixture of nitrogen and oxygen), or any other gas provided that the gas is VOC-free.

Figure 2:
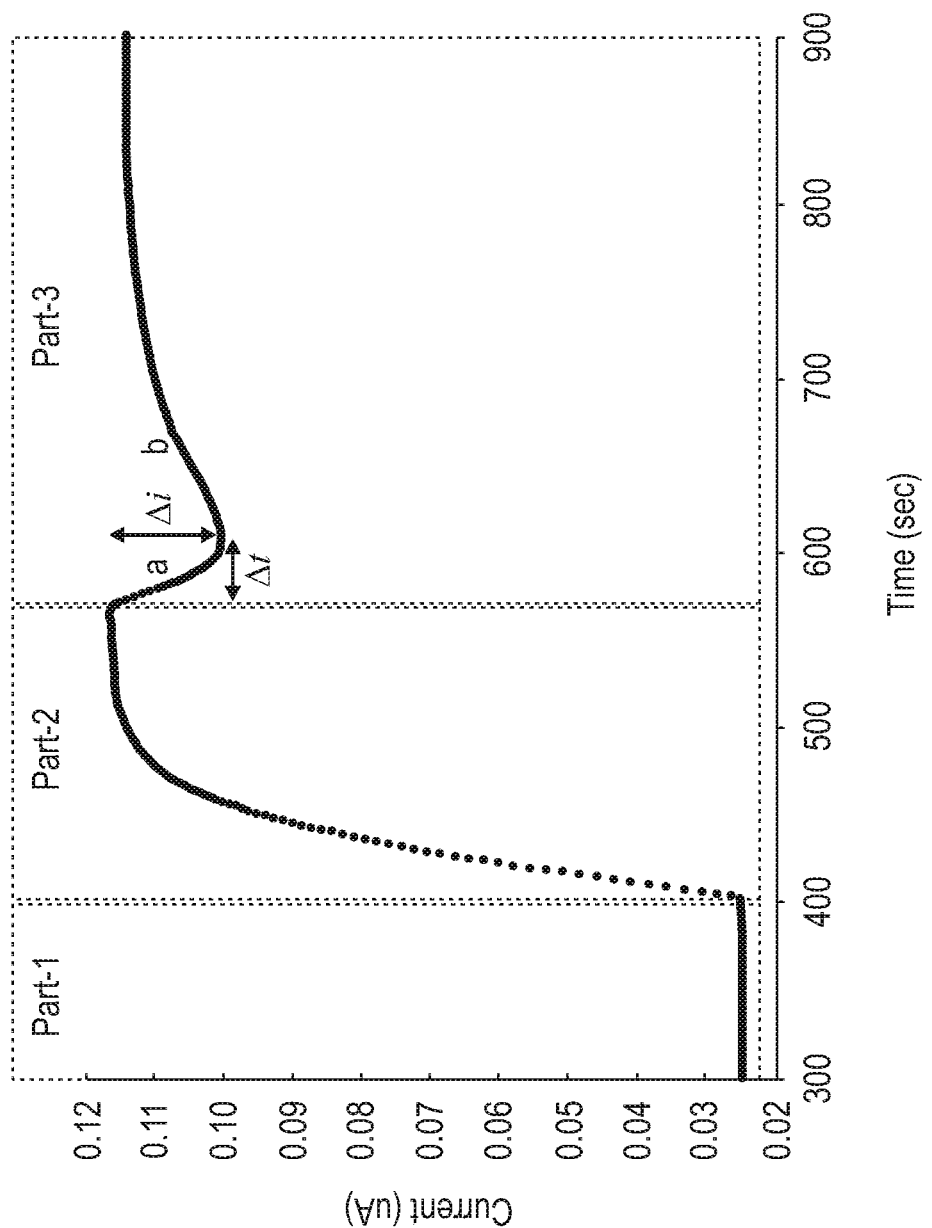
FIG. 2 is a graph showing the three separate parts of an adsorption/desorption profile produced from an AD sensor.

With reference to FIG. 1, when line 1 is open and line 2 is closed, a gas introduced into the AD sensor bypasses the CMM chamber and contacts the gas detector in the detector chamber before exiting the AD sensor. With reference to FIG. 2, Parts 1 and 2 show the electronic signal activity of the AD sensor when line 1 is open and line 2 is closed. Part 1 shows the value when a baseline gas (such as dry air) is introduced into the AD sensor. At time=300-400 sec, the signal generated by the gas detector is parallel to the x-axis with no detectable slope. Part 2 shows the electronic signal activity when a gas of interest (such as a VOC) is introduced into the AD sensor. At time=400-approximately 575 sec, the electronic signal generated by the gas detector increases until the slope reaches an extremum (the Part 2 extremum or influx extremum) at which time the signal becomes parallel to the x-axis. The increasing slope shown at Part 2 corresponds to the presence of a VOC in a sample.

Returning to FIG. 1, when line 1 is closed and line 2 is open, the gas contacts the CMM chamber prior to contact with the gas detector in the detector chamber. With reference to FIG. 2, Part 3, the introduction of the gas into the CMM chamber results in adsorption of the gas by the CMM, which results in a signal decrease at the gas detector. The gas detector signal continues to decrease until the CMM is completely saturated with the gas (the Part 3 extremum or adsorption extremum) at which time, the incoming gas passes through the CMM chamber and comes in contact with the gas detector, which results in a concomitant slow increase in signal as the gas desorbs from the CMM and the gas detector slowly regains its response towards the influx extremum. It is to be understood that not all of the gas entering into the CMM chamber may adsorb onto the CMM and that the amount of gas that adsorbs onto the CMM may be the same as or different to the amount of gas that is subsequently desorbed from the CMM. The amount of gas adsorbed and desorbed will be dependent on the saturation capacity of the CMM. Turning back to FIG. 2, the following characteristics of Part 3 allow for the discrimination of different gases: (1) the initial slope of the signal (a); (2) the duration of time for the plot to reach the adsorption extremum ($\Delta t$); (3) the difference between the detector signal (value at the y-axis) at the onset of Part 3 and that of the adsorption extremum ($\Delta i$); and (4) the slope of the signal from the time it reaches the adsorption extremum until it matches with the influx extremum (b). Each of the four features of Part 3 depend on the interaction between the CMM and the gas resulting in distinguishable Part 3 features for different gases and/or CMMs.

As the gases pass through the CMM and arrive at the detector chamber unhindered, the AD sensor has the ability to detect different gases with the same CMM because the chemical and/or structural differences of the individual VOCs are recognized differently by the chemical and structural aspects of the pores of a CMM. The result is a unique adsorption/desorption profile for every gas that passes through an AD sensor equipped with the same CMM; thus, the adsorption/desorption profiles for VOCs such as ethanol, isopropanol, methanol, acetone, and any combination of the foregoing will all be different from each other.

Figure 3A:
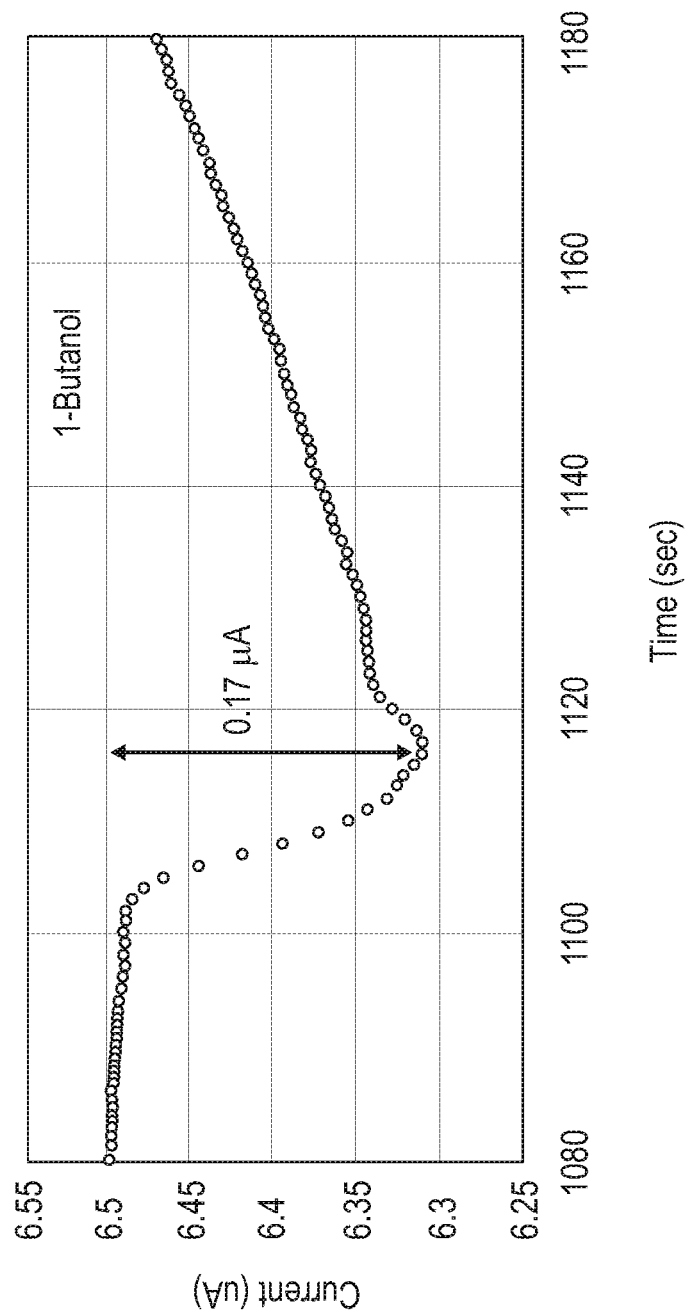
FIGS. 3A-3C are graphs showing the adsorption/desorption profiles of 1-butanol (FIG. 3A), isopropanol (FIG. 3B) and ethanol (FIG. 3C) with the metal organic framework (MOF), Mg-MOF-74.
Figure 3B:
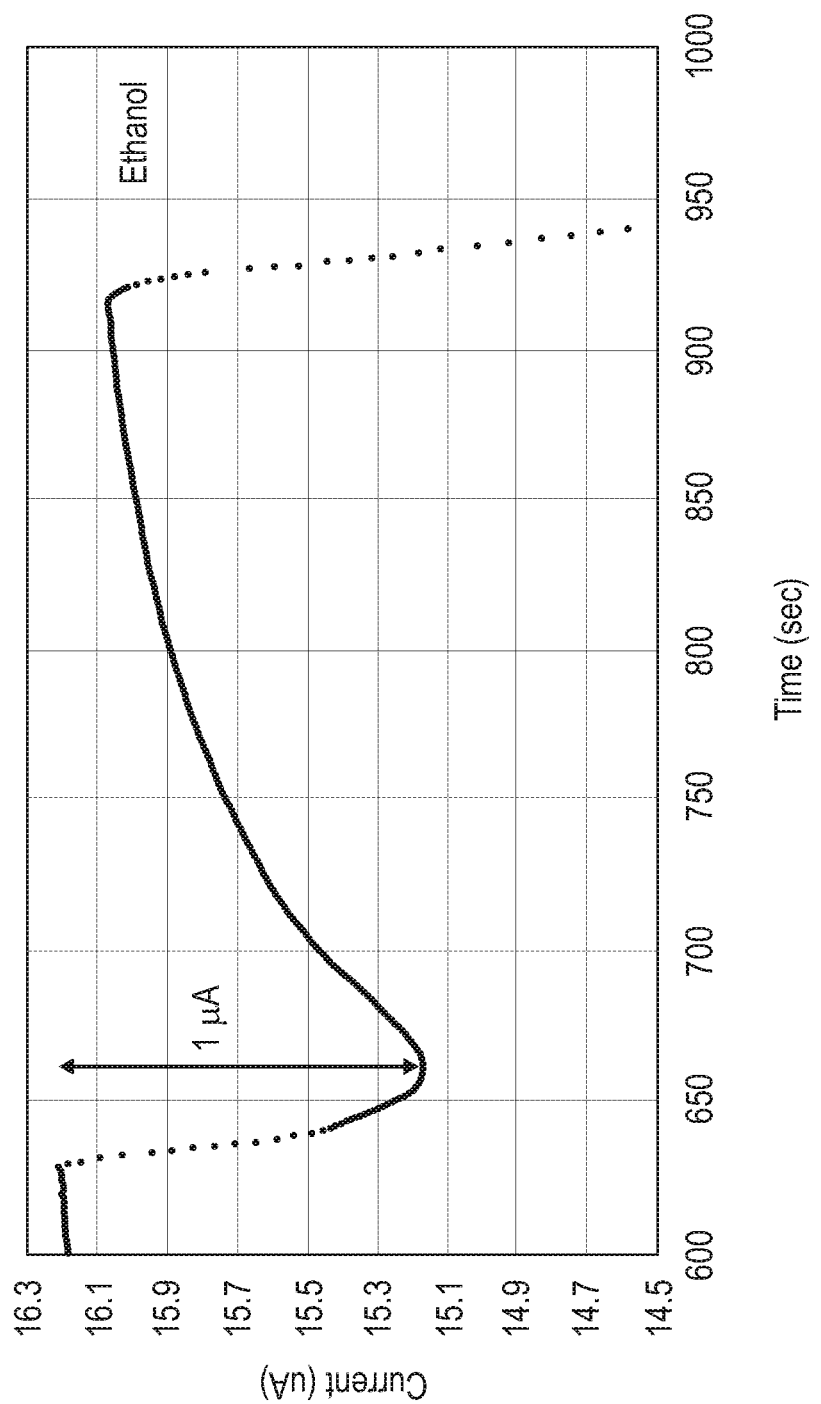
Figure 3C:
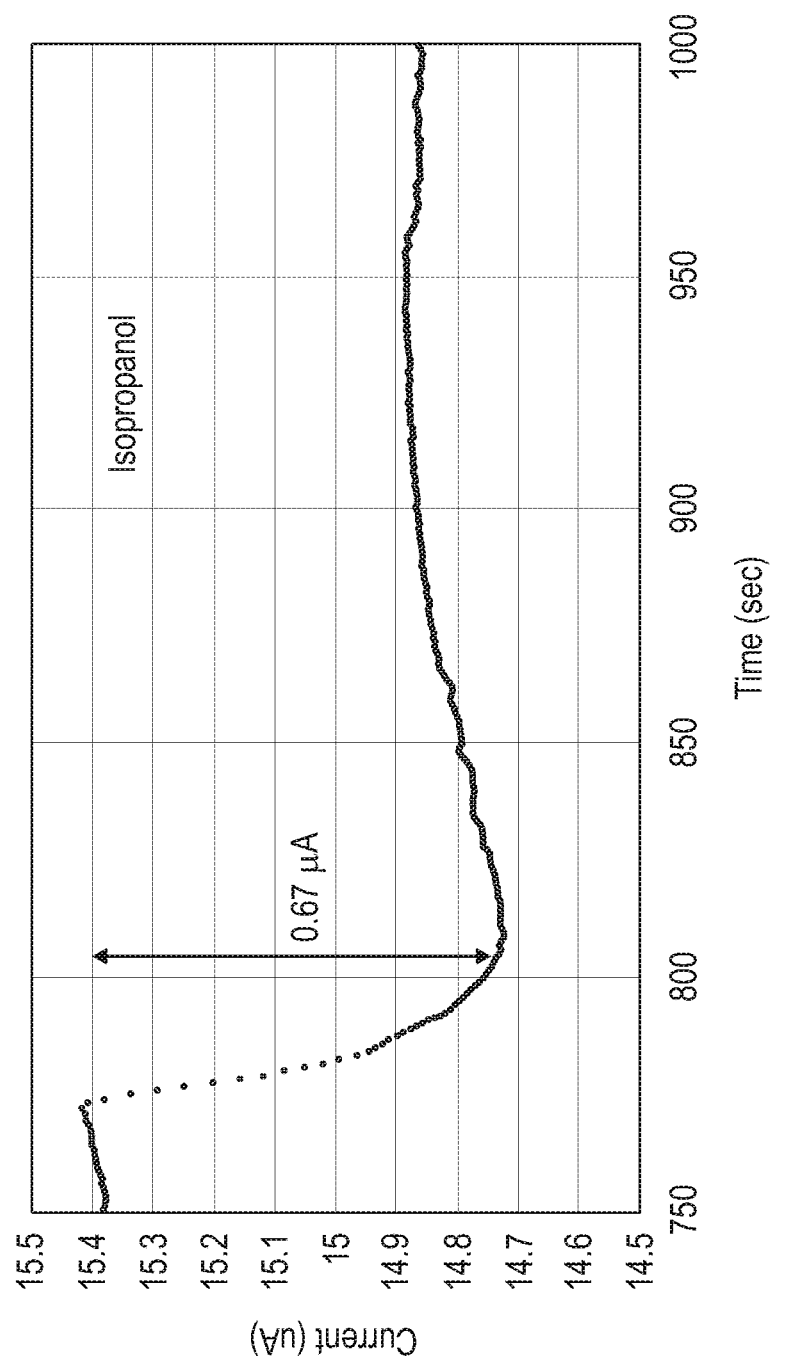

FIGS. 3A-3C show the Part 3 profiles for ethanol (FIG. 3A), isopropanol (FIG. 3B), and 1-butanol (FIG. 3C)— alcohols that differ by one methylene ($-CH_2-$) group— run through the AD sensor with the MOF, Mg-MOF-74 (made internally pursuant to procedures known in the art) as the CMM and a MOxTF as the gas detector (Example 1). As shown in FIGS. 3A-3C, the $\Delta i$ values for the three alcohols are 0.17 µA for 1-butanol, 0.67 µA for isopropanol, and 1 µA for ethanol. The difference in the $\Delta i$ values are due to the Mg-MOF-74 having differential adsorption for the three different alcohols. The signal in the MOxTF detector resulting from the differential adsorption of the three alcohols in the CMM chamber allows these three similar alcohols to be readily discerned from each other from within a single sample.

Figure 4:
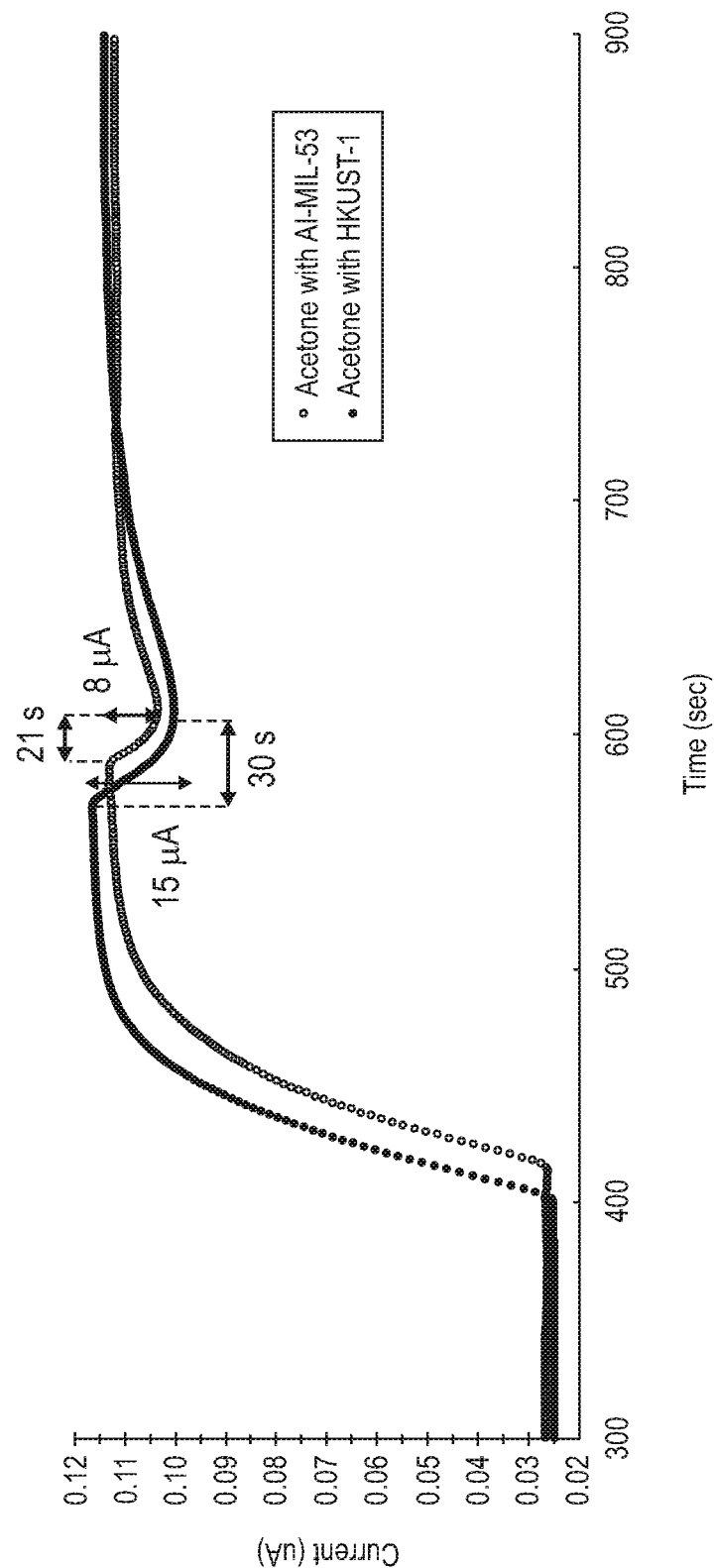
FIG. 4 is a graph showing the adsorption/desorption profiles of acetone and ethanol with the MOF, Al-MIL-53.

FIG. 4 shows the results of the introduction of the VOCs acetone and ethanol run through the AD sensor equipped with the MOF, Al-MIL-53 (aluminum terephthalate, BASF, Ludwigshafen, Germany) as the CMM and a MOxTF as the gas detector (Example 2). As shown in FIG. 4, the two VOCs have identical Part 1 values and similar, but distinct, Part 2 and Part 3 profiles. The Part 3 profiles show Δt (time) and Δi (current) values of 21 sec and 8 µA, respectively, for acetone; and Δt and Δi values of 30 sec and 15 µA, respectively, for ethanol. The results of FIG. 4 demonstrate the sensitivity and selectively of the AD sensor for similar gases analyzed with the same CMM.

Figure 5:
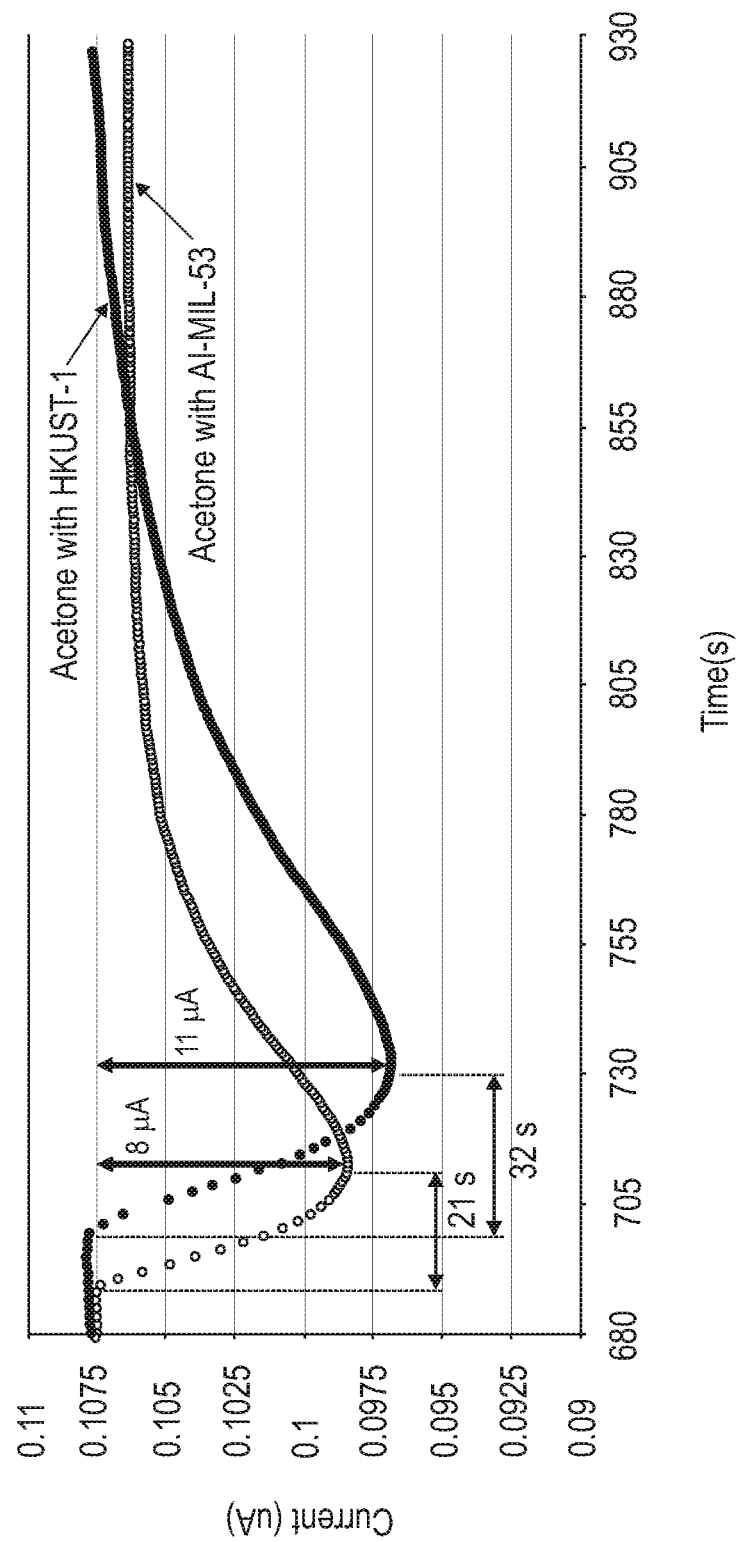
FIG. 5 is a graph showing the adsorption/desorption profile of acetone with two different MOFS, Al-MIL-53 and HKUST-1.

FIG. 5 shows the Part 3 profiles for the VOC, acetone, run through the AD sensor with two separate MOFs as the CMMs; specifically, Al-MIL-53 and HKUST-1 (copper benzene-1,3,5-triccarboxylate, BASF, Ludwigshafen, Germany) and a MOxTF as the gas detector (Example 3). As shown in FIG. 5, the Part 3 desorption profiles show Δt and Δi values of 21 sec and 8 µA, respectively, for acetone/Al-MIL-53; and Δt and Δi values of 32 sec and 11 µA, respectively, for acetone/HUSKT-1. The results of FIG. 5 show that different CMMs can produce distinct Part 3 profiles for the same gas. As noted above, the differing profiles for the same gas with the different CMMs are due to the chemical/structural relationship between the gas and the particular porous structure of the CMM. AD sensors equipped with multiple MOFs can selectively discriminate a wide variety of gases (including VOCs) with very high sensitivity.

Figure 6:
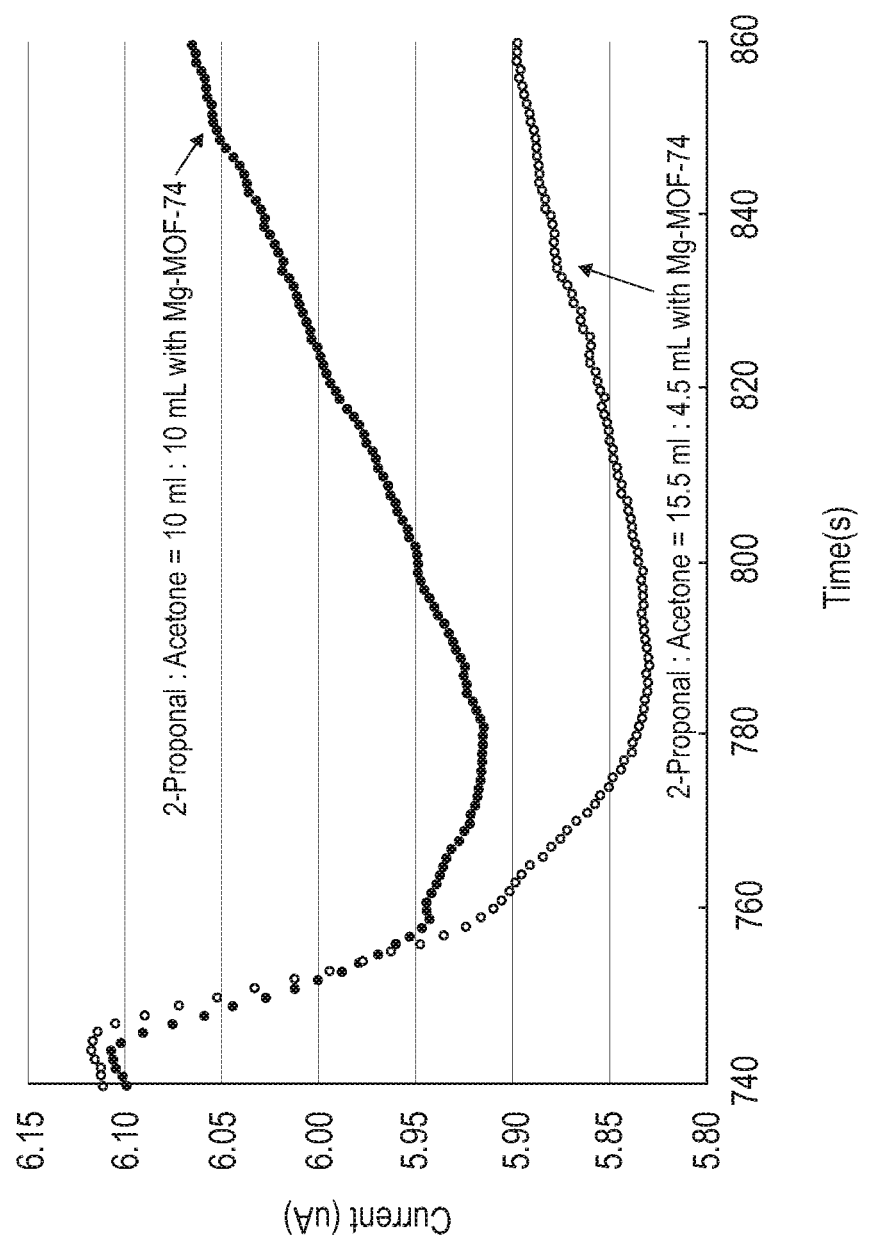
FIG. 6 is a graph showing the adsorption/desorption profiles for a 1:1 mixture and a 3:1 mixture of isopropanol:acetone with the MOF, Mg-MOF-74.
Figure 7:
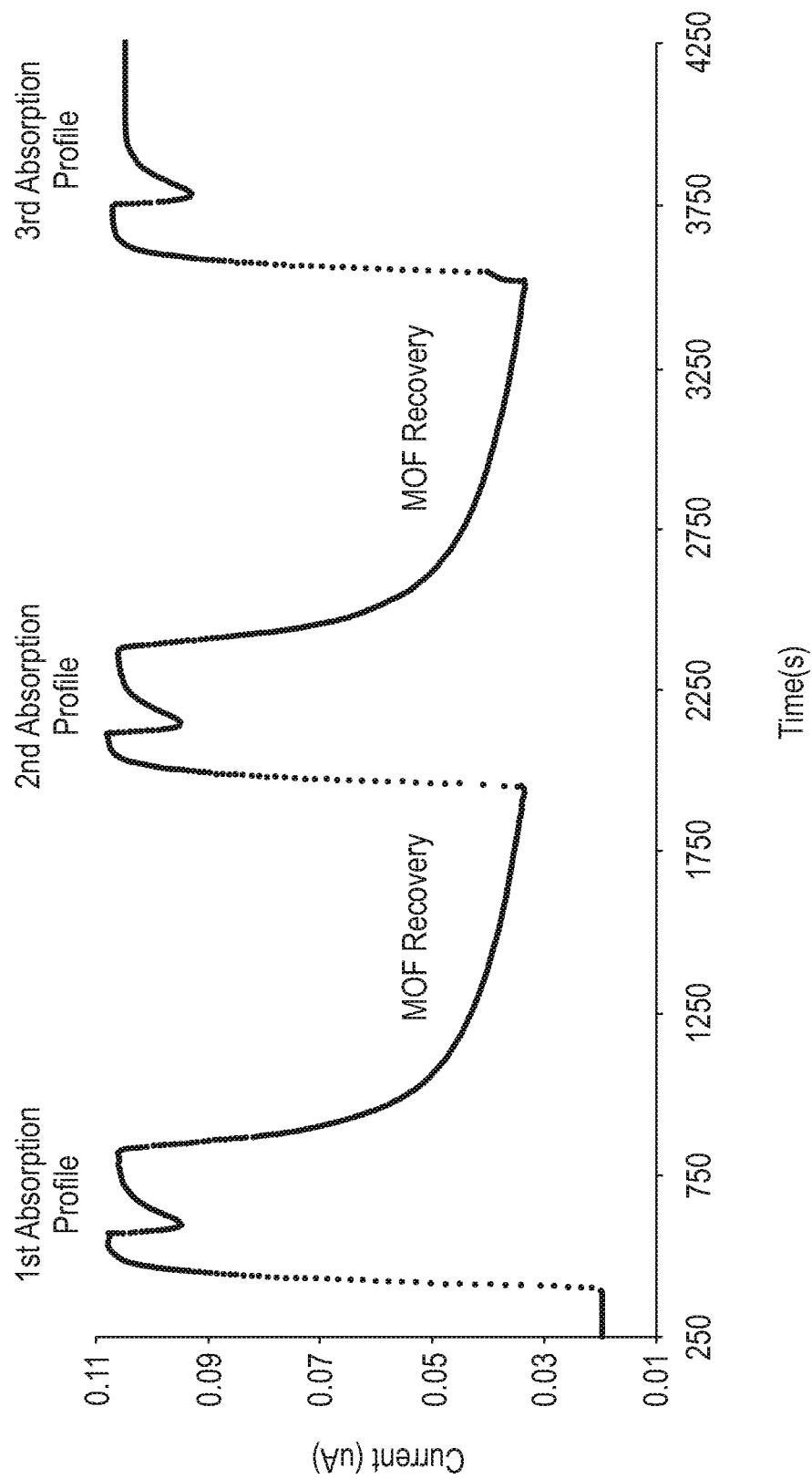
FIG. 7 is a graph showing the recovery profile for the MOF, Mg-MOF-74.

The AD sensor described herein is also capable of distinguishing individual VOC concentrations from a mixture of VOCs. FIG. 6 shows two different Part 3 profiles for isopropanol:acetone (1:1) and isopropanol:acetone (3:1) run through the AD sensor with Mg-MOF-74 as the CMM and a MOxTF as the gas detector (Example 4).

Where the CMM chamber is equipped with a MOF, the MOF may be recovered by heating the chamber to a temperature between 25-500° C. in a flow of analyte-free air (i.e., with no gases or VOCs). At temperatures above 500° C., the morphology of a thin-film MOF may change; thus, the temperature tolerance of a particular MOF should be known prior to attempting a MOF recovery. FIG. 7 shows the recovery profile of a MOF from the CMM chamber of an AD sensor (Example 5). In FIG. 7, the VOC, ethanol, was run through the first and second chambers of the AD sensor through line 2 (line 1 closed) with the MOF, Al-MIL-53, in the first chamber for several runs one after the other. After each run, the influx of the VOC was stopped and dry air was introduced into the CMM chamber with heating to 100° C. to accelerate removal of the VOC and bring the MOF back to its original state. After heating, the MOF was completely desorbed of the VOC and was ready to measure another VOC sample.

The AD sensor described herein has application in a variety of industries, including, without limitation, the food industry to identify the onset of food spoilage and the wine industry to identify the time for bottling. The AD sensor also has utility in identifying harmful VOCs that may be contributing to pollution and/or unsafe workplace conditions. The portable nature of the AD sensor allows the sensor to be useful for field use outside of a laboratory setting.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

EXPERIMENTAL

The following examples are set forth to provide those of ordinary skill in the art with a complete disclosure of how to make and use the aspects and embodiments of the invention as set forth herein. While efforts have been made to ensure accuracy with respect to variables such as amounts, temperature, etc., experimental error and deviations should be taken into account. Unless indicated otherwise, parts are parts by weight, temperature is degrees centigrade, and pressure is at or near atmospheric. All components were obtained commercially unless otherwise indicated.

EXAMPLE 1

Detection of 1-Butanol, Isopropanol, and Ethanol

The AD sensor was set up according to the schematic shown in FIG. 1 with 7 mg of the MOF, Mg-MOF-74, in the CMM chamber and $SnO_2$ as the MOxTF in the detector chamber. A baseline value for the MOxTF was established by running dry air through line 1 at a rate of 50 sccm/min. The same rate of total influx was maintained for the introduction of the VOCs, 1-butanol, isopropanol, and ethanol, but with 45 sccm/min of dry air alone and 5 sccm/min of dry air saturated with the respective VOC. The graphs of the electrical output from the MOxTF for the 1-butanol, isopropanol, and ethanol runs are shown in FIGS. 3A-3C.

1-butanol (FIG. 3A) was introduced into the AD sensor by running a stream of dry air alone at 45 sccm/min plus dry air saturated with 1-butanol at 5 sccm/min with line 1 open and line 2 closed until the signal from the MOxTF increased from the baseline value (where the signal is parallel to the x-axis in FIG. 3A) to the influx extremum (where the signal is also approximately parallel to the x-axis in FIG. 3A). After reaching the influx extremum (which occurred at ~1105 sec and a current of ~6.49 µA), line 1 was closed and line 2 was opened to allow the 1-butanol to adsorb onto the MOF. The adsorption extremum occurred 10 seconds later (at ~1115 sec and a current of ~6.32 µA). The difference in current between the influx extremum and the adsorption extremum was ~0.17 µA. After the adsorption extremum was reached, the flow of the 1-butanol proceeded to pass through the CMM chamber and into the MOxTF detector resulting in a current increase. When the Part 3 profile reached close to the same level as the influx extremum (~65 sec later at ~1180 sec), the influx of 1-butanol was stopped and dry air was run through line 2 until the 1-butanol had desorbed from the MOF (the desorption is not shown in FIG. 3A).

After the 1-butanol run was complete, the Mg-MOF-74 was recovered (Example 5), a new baseline was established (using dry air), and isopropanol (FIG. 3B) was introduced into the AD sensor by running a stream of dry air alone at 45 sccm/min plus dry air saturated with isopropanol at 5 sccm/min with line 1 open and line 2 closed until the influx extremum was reached (at ~775 sec and a current of ~15.40 µA). After reaching the influx extremum, line 1 was closed and line 2 was opened to allow the isopropanol to adsorb onto the MOF. The adsorption extremum occurred 35 seconds later (at ~810 secs and at a current of ~14.73 µA). The difference in current between the influx extremum and the adsorption extremum was ~0.67 µA. After the adsorption extremum was reached, the flow of the isopropanol proceeded to pass through the CMM chamber and into detector chamber resulting in a current increase. When the Part 3 profile became parallel to the x-axis, the influx of isopropanol was stopped and dry air was run through line 2 until the isopropanol had desorbed from the MOF. The adsorption behavior of isopropanol was found to be unique in that the Part 3 profile did not approach the same level as the influx extremum.

After the isopropanol run was complete, the Mg-MOF-74 was recovered (Example 5), a new baseline was established (using dry air), and ethanol (FIG. 3C) was introduced into the AD sensor by running a stream of dry air alone at 45 sccm/min plus dry air saturated with ethanol at 5 sccm/min with line 1 open and line 2 closed until the influx extremum was reached (at ~630 sec and a current of ~16.2 µA). After reaching the influx extremum, line 1 was closed and line 2 was opened to allow the ethanol to adsorb onto the MOF. The adsorption extremum occurred 30 second later (at ~660 sec and a current of ~15.2 µA). The difference in current between the influx extremum and the adsorption extremum was ~1 µA. After the adsorption extremum was reached, the flow of the ethanol proceeded to pass through the CMM chamber and into the detector chamber resulting in a current increase. When the Part 3 profile reached close to the same level as the influx extremum (~260 sec later at ~920 sec), the influx of ethanol was stopped and dry air was run through line 2 at 120 sccm/min until the ethanol had desorbed from the MOF (shown in FIG. 3C as the current drop between ~925-935 sec).

EXAMPLE 2

Detection of Acetone and Ethanol

The AD sensor was set up according to the schematic in FIG. 1 with 25 mg of the MOF, Al-MIL-53, in the CMM chamber and SnO$_2$ as the MOxTF in the detector chamber. A baseline value for the MOxTF was established by running dry air through line 1 at a rate of 50 sccm/min. The same rate of total influx was maintained for the introduction of the VOCs, acetone and ethanol, but with 45 sccm/min of dry air alone and 5 sccm/min of dry air saturated with the respective VOC.

Acetone was introduced into the AD sensor by running a stream of dry air alone at 45 sccm/min plus dry air saturated with acetone at 5 sccm/min with line 1 open and line 2 closed until the influx extremum was reached (at ~589 sec and current of ~0.112 mA). After reaching the influx extremum, line 1 was closed and line 2 was opened to allow the acetone to adsorb onto the MOF. The adsorption extremum occurred 21 seconds later (at ~610 sec and a current of ~0.104 mA). The difference in current between the influx extremum and the adsorption extremum was ~8 µA. After the adsorption extremum was reached, the flow of the acetone proceeded to pass through the CMM chamber and into the detector chamber resulting in a current increase. When the Part 3 profile reached close to the same level as the influx extremum (~50 seconds later at ~660 sec), the influx of acetone was stopped and dry air was run through line 2 until the acetone had desorbed from the MOF.

After the acetone run was complete, the Al-MIL-53 was recovered (Example 5), a new baseline was established (using dry air), and ethanol was introduced into the AD sensor by running a stream of dry air alone at 45 sccm/min plus dry air saturated with ethanol at 5 sccm/min with line 1 open and line 2 closed until the influx extremum was reached (at ~575 sec and a current of ~0.115 mA). After reaching the influx extremum, line 1 was closed and line 2 was opened to allow the ethanol to adsorb onto the MOF. The adsorption extremum occurred 30 seconds later (at ~605 secs and a current of ~0.100 mA). The difference in current between the influx extremum and the adsorption extremum was ~15 µA. After the adsorption extremum was reached, the flow of the ethanol proceeded to pass through the CMM chamber and into the detector chamber resulting in a current increase. Once the Part 3 profile reached close to the same level as the influx extremum (~145 seconds later at ~775 sec), the influx of ethanol was stopped and dry air was run through line 2 until the acetone had desorbed from the MOF.

The results of the acetone and ethanol runs are shown in FIG. 4.

EXAMPLE 3

Detecting Acetone With Two Different MOFS

The AD sensor was set up according to the schematic in FIG. 1 with 25 mg of the MOF, Al-MIL-53, in the CMM chamber and SnO$_2$ as the MOxTF in the detector chamber. A baseline value for the MOxTF was established by running dry air through line 1 at a rate of 50 sccm/min. Using the same rate of total influx, acetone was introduced into the AD sensor by running a stream of dry air alone at 45 sccm/min plus dry air saturated with acetone at 5 sccm/min with line 1 open and line 2 closed until the influx extremum was reached (at ~689 sec and a current of ~0.1075 mA). After reaching the influx extremum, line 1 was closed and line 2 was opened to allow the acetone to adsorb onto the Al-MIL-53. The adsorption extremum occurred 21 seconds later (at ~710 sec and a current of ~0.0995 mA). The difference in current between the influx extremum and the adsorption extremum was ~8 µA. After the adsorption extremum was reached, the flow of the acetone proceeded to pass through the CMM chamber and into the detector chamber resulting in a current increase. Once the Part 3 profile reached close to the same level as the influx extremum (~120 seconds later at ~830 sec), the influx of acetone was stopped and dry air was run through line 2 until the acetone had desorbed from the Al-MOF-53.

After the acetone run on the Al-MOF-53 was complete, the CMM chamber was cleared of the Al-MOF-53 and replaced with 25 mg of the MOF, HKUST-1. A baseline value for the MOxTF detector was again established by running dry air through line 1 at a rate of 50 sccm/min followed by the introduction of acetone into the AD sensor as described above. With HKUST-1 as the MOF, the influx extremum (line 1 closed, line 2 open) was reached at ~700 seconds (at a current of ~0.108 mA). After reaching the influx extremum, line 1 was closed and line 2 was opened to allow the acetone to adsorb onto the HKUST-1. The adsorption extremum occurred 32 seconds later (at ~732 sec and a current of ~0.0970 mA). The difference in current between the influx extremum and the adsorption extremum was ~11 µA. After the adsorption extremum was reached, the flow of the acetone proceeded to pass through the CMM chamber and into the detector chamber resulting in a current increase. Once the Part 3 profile reached close to the same level as the influx extremum (~198 seconds later at ~930 sec), the influx of acetone was stopped and dry air was run through line 2 until the acetone had desorbed from the HKUST-1.

The results of the two acetone runs with the two different MOFS are shown in FIG. 5.

EXAMPLE 4

Distinguishing 1:1 and 3:1 Isopropanol:Acetone Mixtures

The AD sensor was set up according to the schematic in FIG. 1 with 7 mg of the MOF, Mg-MOF-74, in the CMM chamber and $SnO_2$ as the MOxTF in the detector chamber. A baseline value for the MOxTF was established by running dry air through line 1 at a rate of 50 sccm/min. The same rate of total influx was maintained for the introduction of the VOC mixtures, 1:1 isopropanol:acetone and 3:1 isopropanol:acetone, but with 45 sccm/min of dry air alone and 5 sccm/min of dry air saturated with the respective VOC mixtures.

A 20 mL sample of 1:1 isopropanol:acetone (10 mL:10 mL; hereinafter "1:1 sample") was introduced into the AD sensor by running a stream of dry air alone at 45 sccm/min plus dry air saturated with the 1:1 sample at 5 sccm/min with line 1 open and line 2 closed until the influx extremum was reached (at ~745 seconds and a current of ~61.1 µA). After reaching the influx extremum, line 1 was closed and line 2 was opened to allow the 1:1 sample to adsorb onto the MOF. The adsorption extremum occurred ~35 seconds later (at ~780 sec and a current of ~59.2 µA). The difference in current between the influx extremum and the adsorption extremum was ~1.9 µA. After the adsorption extremum was reached, the flow of the 1:1 sample proceeded to pass through the CMM chamber and into the detector chamber resulting in a current increase. Once the Part 3 profile reached close to the same level as the influx extremum (~80 seconds later at ~860 sec), the influx of the 1:1 sample was stopped and dry air was run through line 2 until the 1:1 sample had desorbed from the MOF.

After the run of the 20 mL 1:1 sample was complete, the Mg-MOF-74 was recovered (Example 5), a new baseline was established (using dry air), and a 20 mL sample of 3:1 isopropanol:acetone (hereinafter "3:1 sample") was introduced into the AD sensor by running a stream of dry air alone at 45 sccm/min plus dry air saturated with the 1:3 sample at 5 sccm/min with line 1 open and line 2 closed until the influx extremum was reached (at ~747 sec and a current of ~61.3 µA). After reaching the influx extremum, line 1 was closed and line 2 was opened to allow the acetone to adsorb onto the MOF. The adsorption extremum occurred 38 seconds later (at ~785 sec and a current of ~58.3 µA). The difference in current between the influx extremum and the adsorption extremum was ~3 µA. After the adsorption extremum was reached, the flow of the 3:1 sample proceeded to pass through the CMM chamber and into the detector chamber resulting in a current increase. Once the Part 3 profile started becoming parallel to x-axis, the influx of the 1:3 sample was stopped and dry air was run through line 2 until the 3:1 sample had desorbed from the MOF.

The results of the two separate runs are shown in FIG. 6. As shown therein, the adsorption behavior of the 3:1 isopropanol:acetone sample (but not the lower concentration 1:1 isopropanol:acetone sample) exhibited a similar Part 3 profile as was seen with the pure isopropanol sample from Example 1 (FIG. 3B).

EXAMPLE 5

MOF Recovery

The AD sensor was set up according to the schematic in FIG. 1 with 25 mg of the MOF, Al-MIL-53, in the CMM chamber and $SnO_2$ as the MOxTF in the detector chamber. A baseline value for the MOxTF was established by running dry air through line 1 at a rate of 50 sccm/min. Using the same rate of total influx, ethanol was introduced into the AD sensor by running a stream of dry air alone at a rate of 45 sccm/min plus dry air saturated with ethanol at a rate of 5 sccm/min with line 1 open and line 2 closed until the influx extremum was reached, at which time, line 1 was closed and line 2 was opened to allow the ethanol to adsorb onto the MOF. After the adsorption extremum occurred, the flow of the ethanol proceeded to pass through the CMM chamber and into the detector chamber resulting in a current increase. When the desorption profile reached close to the same level as the influx extremum, the Al-MIL-53 was recovered by heating the Al-MIL-53 to 100° C. while passing a stream of dry air at 120 sccm/min. The Al-MIL-53 recovered to its original state ~1200 seconds (~20 minutes) later. Upon recovery of the Al-MIL-53, ethanol was run through the AD sensor in an identical run and the second recovery of the Al-MIL-53 also took ~20 minutes.

The results of the two separate Al-MIL-53 recovery runs are show in FIG. 7.

We claim:

1. A method of detecting at least one volatile organic compound (VOC), comprising the steps of:
   providing a first chamber and a second chamber connected in series, wherein the first chamber contains a porous material that adsorbs at least one VOC and the second chamber contains a detector for detecting a presence and concentration of the at least one VOC;
   introducing a gas without the at least one VOC into the second chamber while bypassing the first chamber;
   establishing a first baseline electronic signal corresponding to the gas without the at least one VOC, wherein the first baseline electronic signal is generated by the detector in the second chamber;
   introducing at least one VOC into the second chamber while bypassing the first chamber;
   detecting, over time, the presence of the at least one VOC in the second chamber by establishing a second electronic signal corresponding to the concentration of the at least one VOC in the second chamber, wherein the second electronic signal is generated by the detector in the second chamber;
   re-routing the gas so that it is directed into the first chamber, wherein an amount of the at least one VOC is adsorbed onto the porous material in the first chamber;
   directing the re-routed gas out of the first chamber into the second chamber; and
   monitoring, over time, a third electronic signal corresponding to a change in the concentration of the VOC in the first chamber resulting from adsorption of some or all of the at least one VOC and subsequent desorption of some or all of the at least one VOC, wherein the third electronic signal is generated by the detector in the second chamber; and
   comparing the third electronic signal with electronically stored signals for known VOCs, thereby identifying the at least one VOC, wherein the third electronic signal reaches an extremum as the amount of the at least one VOC adsorbed in the first chamber no longer increases, and upon desorption of the at least one VOC from the first chamber, the third electronic signal approaches a background level equal to a maximum value of the second electronic signal.

2. The method of claim 1, wherein each of the steps is carried out in turn.

3. The method of claim 1, wherein the porous material is selected from the group consisting of a metal organic framework, a covalent organic framework, a metal-organic polyhedral, a coordination polymer, zeolites, microporous carbonaceous materials, and combinations thereof.

4. The method of claim 1, wherein the porous material comprises a metal organic framework.

5. The method of claim 1, wherein the first chamber further comprises a heating plate.

6. The method of claim 1, wherein the porous material is recycled by heating the first chamber to a temperature that does not alter the structure of the porous material.

7. The method of claim 1, wherein the detector in the second chamber is selected from the group consisting of a gas chromatography mass spectrometer, an infra-red spectrophotometer, an electrochemical sensor, a quartz crystal microbalance, a metal oxide semiconductor, and combinations thereof.

8. The method of claim 1, wherein the detector in the second chamber comprises a metal oxide thin film.

9. The method of claim 1, wherein the detector in the second chamber is deposited on a membrane heater fitted with microelectrodes.

10. A system comprising:
a first chamber comprising a crystalline microporous material for adsorbing and desorbing at least one gas;
a second chamber comprising a gas detector for detecting and measuring a concentration of the least one gas;
a pass-through line comprising an input, a first line, and a second line, wherein the first line bypasses the first chamber and passes through the second chamber, and the second line passes through the first and second chambers,
wherein upon entry of the at least one gas into the system, the at least one gas is routed to the second chamber via the input and the first line, wherein the gas detector in the second chamber generates a signal over time corresponding to the concentration of the at least one gas in the second chamber, and
wherein the at least one gas is rerouted from the second chamber to the first chamber via the input and the second line, wherein an amount of the at least one gas is adsorbed onto the crystalline microporous material and then some or all of the amount of the at least one gas is desorbed from the crystalline microporous material, and the gas detector in the second chamber generates a signal over time corresponding to the concentration of the at least one gas in the first chamber that is not adsorbed onto the crystalline microporous material.

11. The system of claim 10, wherein the at least one gas is a volatile organic compound.

12. The system of claim 10, wherein the crystalline microporous material is selected from the group consisting of a metal organic framework, a covalent organic framework, a metal-organic polyhedral, a coordination polymer, zeolites, microporous carbonaceous materials, and combinations thereof.

13. The system of claim 10, wherein the crystalline microporous material comprises a metal organic framework.

14. The system of claim 10, wherein the first chamber further comprises a heating plate.

15. The system of claim 14, wherein the crystalline microporous material is recycled by heating the first chamber to a temperature that does not alter the structure of the crystalline microporous material.

16. The system of claim 10, wherein the gas detector in the second chamber is selected from the group consisting of a gas chromatography mass spectrometer, an infra-red spectrophotometer, an electrochemical sensor, a quartz crystal microbalance, a metal oxide semiconductor, and combinations thereof.

17. The system of claim 10, wherein the gas detector in the second chamber comprises a metal oxide thin film.

18. The system of claim 10, wherein the metal oxide thin film is deposited on a membrane heater fitted with microelectrodes.

19. A system comprising:
a first chamber comprising a crystalline microporous material for adsorbing and desorbing at least one gas;
a second chamber comprising a gas detector for detecting and measuring a concentration of the least one gas;
a pass-through line comprising,
an input,
an output,
a first line that bypasses the first chamber and runs from the input to the output via the second chamber, and
a second line that passes from the input through the first and second chambers to the output,
wherein upon entry of the at least one gas into the system via the input, the at least one gas is (i) routed to the second chamber via the first line, wherein the at least one gas is detected, and (ii) rerouted to the first chamber via the second line, wherein an amount of the at least one gas is adsorbed onto the microporous crystalline structure and then some or all of the amount of the at least one gas is desorbed from the microporous crystalline structure,
wherein the gas detector in the second chamber produces a first signal corresponding to the concentration of the at least one gas in the second chamber, a second signal corresponding to the amount of the least one gas adsorbed to the crystalline microporous material in the first chamber, and a third signal corresponding to the amount of the at least one gas desorbed from the crystalline microporous material in the first chamber, wherein the three signals together produce an adsorption/desorption profile for the at least one gas to enable identification of the at least one gas.

20. The system of claim 19, wherein the at least one gas is a volatile organic compound.

21. The system of claim 19, wherein the crystalline microporous material is selected from the group consisting of a metal organic framework, a covalent organic framework, a metal-organic polyhedral, a coordination polymer, zeolites, microporous carbonaceous materials, and combinations thereof.

22. The system of claim 19, wherein the crystalline microporous material comprises a metal organic framework.

23. The system of claim 19, wherein the first chamber further comprises a heating plate.

24. The system of claim 23, wherein the crystalline microporous material is recycled by heating the first chamber to a temperature that does not alter the structure of the crystalline microporous material.

25. The system of claim 19, wherein the gas detector in the second chamber is selected from the group consisting of a gas chromatography mass spectrometer, an infra-red spectrophotometer, an electrochemical sensor, a quartz crystal microbalance, a metal oxide semiconductor, and combinations thereof.

26. The system of claim 19, wherein the gas detector in the second chamber comprises a metal oxide thin film.

27. The system of claim 26, wherein the metal oxide thin film is deposited on a membrane heater fitted with microelectrodes.

* * * * *